(12) United States Patent
Berndt

(10) Patent No.: US 6,180,314 B1
(45) Date of Patent: Jan. 30, 2001

(54) METHOD FOR PREPARING THIN LIQUID SAMPLES FOR MICROSCOPIC ANALYSIS

(75) Inventor: Klaus W. Berndt, Timonium, MD (US)

(73) Assignee: Becton, Dickinson and Company, Franklin Lakes, NJ (US)

(*) Notice: Under 35 U.S.C. 154(b), the term of this patent shall be extended for 0 days.

(21) Appl. No.: 09/085,851

(22) Filed: May 27, 1998

(51) Int. Cl.⁷ .................................................. G02B 21/34
(52) U.S. Cl. ........................ 430/180; 436/174; 436/165; 422/100; 422/104
(58) Field of Search .......................... 436/46, 174, 180, 436/165; 422/55, 57, 58, 68.1, 99, 100, 104; 356/244, 246; 359/398

(56) References Cited

U.S. PATENT DOCUMENTS

| 3,198,064 | * | 8/1965 | Moore | 359/397 |
| 3,447,863 | * | 6/1969 | Patterson | 350/326 |
| 3,551,023 | * | 12/1970 | Brackett | 350/95 |
| 3,572,892 | * | 3/1971 | Metzgar | 350/95 |
| 3,879,106 | * | 4/1975 | McCormick | 350/95 |
| 4,022,521 | * | 5/1977 | Hall et al. | 350/95 |
| 4,260,392 | * | 4/1981 | Lee | 422/56 |
| 4,501,496 | * | 2/1985 | Griffin | 356/246 |
| 4,595,561 | * | 6/1986 | Thornton et al. | 422/58 |
| 5,349,436 | * | 9/1994 | Fisch | 356/246 |
| 5,681,741 | * | 10/1997 | Atwood et al. | 435/287.2 |
| 5,812,312 | * | 9/1998 | Lorincz | 359/397 |
| 5,939,251 | * | 8/1999 | Hu | 435/4 |

* cited by examiner

Primary Examiner—Long V. Le
(74) Attorney, Agent, or Firm—Bruce S. Weintraub

(57) ABSTRACT

The present invention relates to the field of microscopic sample analysis, and specifically relates to a method for preparing thin microscopic samples of liquids.

60 Claims, 11 Drawing Sheets

METHOD FOR PREPARING THIN LIQUID SAMPLES FOR MICROSCOPIC ANALYSIS

FIELD OF THE INVENTION

The present invention relates to the field of microscopic sample analysis, and specifically relates to a method for preparing thin microscopic samples of liquids.

BACKGROUND OF THE INVENTION

Microscopic examination of blood films is an important part of the hematologic evaluation. Today, three methods for preparing thin blood films are in use, namely the "wedge-slide method", the "spinner method" and the "coverglass method" (see, e.g. "Clinical Diagnosis and Management by Laboratory Methods", Nineteenth Edition, 1996, edited by John B. Henry). In the wedge-slide method, a drop of blood is placed onto a slide that is on a flat surface. A second (spreader) slide is pressed at an angle of 30 to 45 degrees against the first slide and moved along the first slide, which results in the formation of a moderately thin blood film that is then dried in air. The quality of the generated blood smear will strongly depend on the personal skill level of the technician. To overcome the need for highly skilled personnel, manual apparatus (U.S. Pat. No. 4,494,479 to Drury) and automated apparatus (U.S. Pat. No. 4,407,843 to Sasaki; U.S. Pat. No. 3,683,850 to Grabhorn; U.S. Pat. No. 3,880,111 to Levine et al.; U.S. Pat. No. 4,392,450 to Prevo; WO 9,641,148 to Levine et al.) for executing the wedge-slide method have been proposed.

In addition to being time-consuming, the physical action of the spreader slide tends to distort the morphology of many of the cells. In view of this, an alternative method for the preparation of blood samples has been proposed (e.g., U.S. Pat. No. 5,549,750 to Kelley) wherein a drop of blood is disposed onto a slide which is then spun to create a monolayer of randomly distributed red blood cells. It has been found, however, that drying of the red blood cells produces undesirable types of distortions, particularly a loss of central pallor for many of the red cells as they dry. It is not entirely clear what causes these shape changes, but they apparently are caused by surface tension, charges and/or drying effects. To inhibit cell morphology distortions from occurring during drying, it has been proposed to preserve the morphologies by applying fixing agents after forming the monolayer, but prior to drying (U.S. Pat. No. 4,209,548 to Bacus; U.S. Pat. No. 4,483,882 to Saunders).

The wedge-slide method as well as the spinner method require relatively complex apparatus and involve time-consuming procedures. A simpler way to produce blood films is the coverglass method where two quadratic cover-glasses are being used. A first glass, with a drop of blood attached to the center of the underside, is placed crosswise on a second glass so that the corners appear as an eight-pointed star. If the drop is not too large and if the glasses are perfectly clean, the blood will spread out evenly and quickly in a thin layer between the two surfaces. After spreading stops, the two glasses are pulled apart on a plane parallel to their surfaces. The two blood films are then dried in air.

While the coverglass method does not require auxiliary apparatus, the quality of the blood smears will again depend strongly on the level of skill of the technician performing the procedure. Moreover, executing the method includes increased risk because the thin pieces of glass that contain the blood sample may break during the separation step. And, finally, drying the blood films may cause changes in the cell morphology.

Consequently, there exists a need for a simple method to produce thin blood samples for microscopic analysis that does not require auxiliary apparatus, provides monolayers of red blood cells, and avoids changes in the cell morphology.

SUMMARY OF THE INVENTION

It is an objective of the present invention to provide a method and device for producing thin samples of liquids for microscopic analysis, and preferably, thin samples of blood, that does not require auxiliary apparatus, provides, in the instance of blood, monolayers of red blood cells, and avoids changes in the cell morphology.

According to the present invention, the above objective is achieved by disposing a drop of a liquid sample, such as, for example, blood, onto a microscope slide near to its center, by arranging spacers on the slide outside of the slide's center, by positioning a flexible coverglass onto the spacers, by applying a downward force to, for example, the center of the flexible coverglass so that the coverglass touches the blood, and by suspending the application of said force. In the moment the coverglass touches the drop of sample, the sample spreads outwards and adhesion forces hold the flexible coverglass down so that a very thin layer of liquid is formed.

According to the invention, it is important that the spread sample fills the space between the slide and the coverglass only partially. This can be accomplished by selecting the height of the spacers accordingly. Preferably, the spacers can have a height of from about 10 micrometers ($\mu$m) to about 3000 $\mu$m, and more preferably from about 50 $\mu$m to about 200 $\mu$m. The coverglass is held in a stable position due to an equilibrium state between said adhesion forces and counter forces generated as a consequence of coverglass bending.

It has been found that a liquid blood sample prepared according to the present invention comprises a central area which contains plasma but no red blood cells. This region is surrounded by a wide ring containing huge numbers of isolated red blood cells in a well-defined monolayer arrangement. The ring in turn is surrounded by an even wider belt that contains red blood cells in Rouleaux formation (blood cell aggregation) where the length of the Rouleaux blocks increases with increasing distance from the center. This kind of blood sample preparation does not result in morphology changes as observed in the wedge-slide method or during drying of blood films in the open air. Due to the coverglass bending, regions of varying sample thickness are available for examination.

Of course, as noted above, the method and device for sample preparation according to the present invention is not limited to blood samples. However, in the following detailed description, the invention will be disclosed in more detail, using blood as a preferred example.

DETAILED DESCRIPTION OF THE INVENTION

According to the present invention, a thin liquid sample for microscopic analysis is prepared by disposing a drop of sample onto a microscope slide near to its center, by arranging spacers on the slide outside of the slide's center, by positioning a flexible coverglass onto the spacers, by applying a downward force to, for example, the center of the flexible coverglass so that the coverglass touches the sample, and by suspending the application of said force. In the moment the coverglass touches the drop of sample, the sample spreads outwards and adhesion forces hold the flexible coverglass down so that a very thin layer of liquid is formed.

Figure 1:
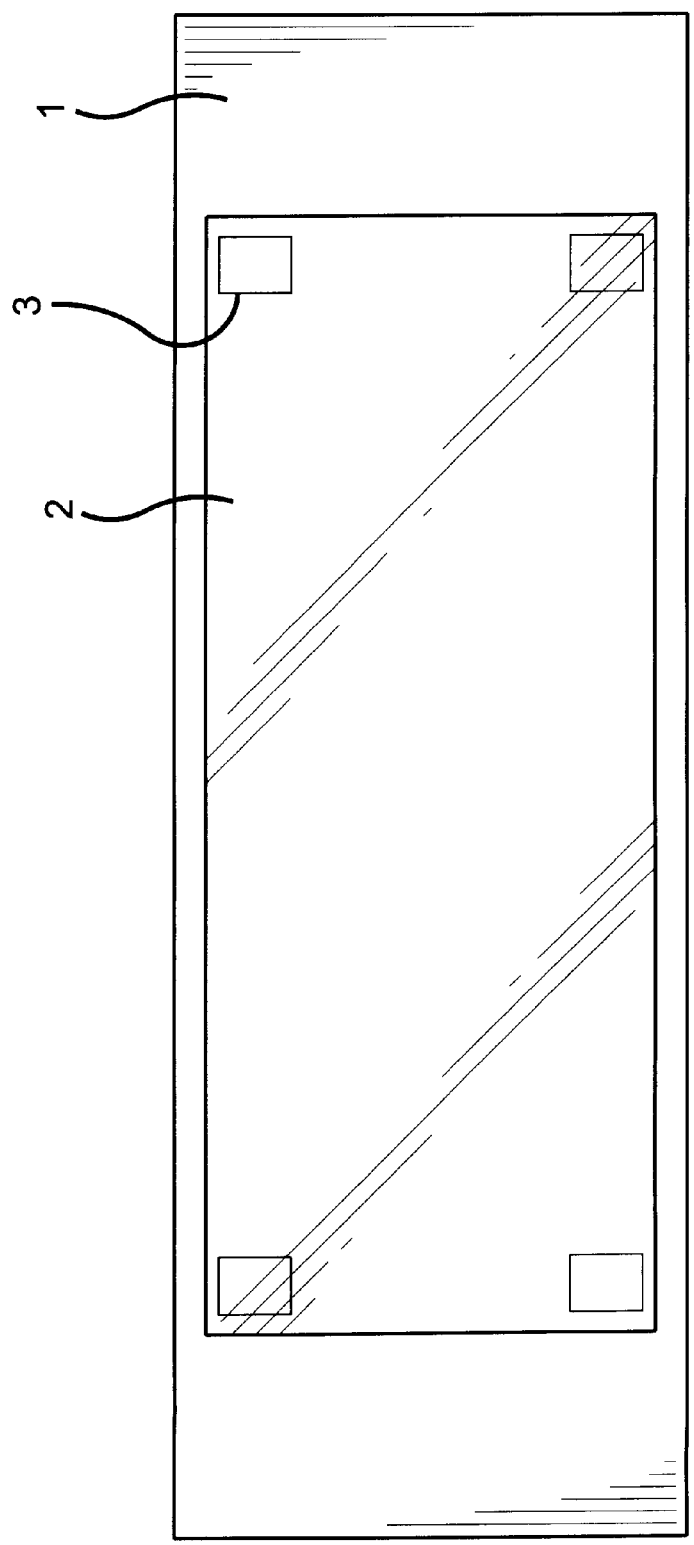
FIG. 1 shows schematically a top plan view of a microscope slide with a coverglass supported by four spacers.
Figure 2:
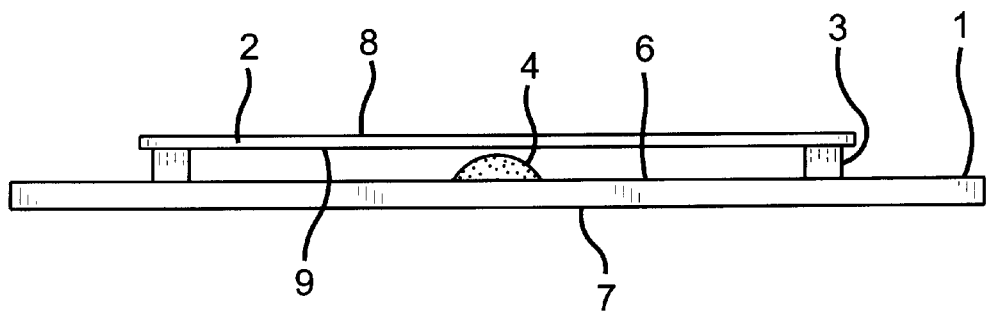
FIG. 2 depicts a side view of the arrangement of FIG. 1 with a drop of blood disposed to the center of the slide.
Figure 3:
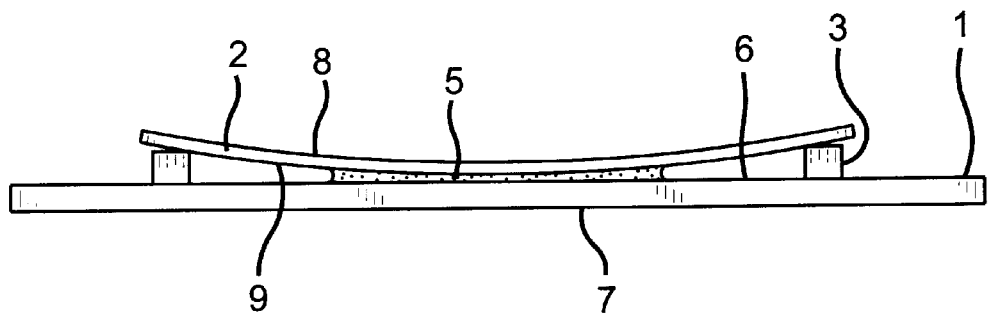
FIG. 3 shows the arrangement of FIG. 2 after applying a downward force to the coverglass and discontinuing the application of this force.

This is illustrated, for example, in FIGS. 1, 2, and 3. The liquid sample, can, in a preferred embodiment, be blood. FIG. 1 shows an example where four spacers (3) are used to hold a coverglass (2) in a parallel position above a microscope slide (1). The height of the spacers (3) is selected so that the coverglass (2) can be positioned on the spacers (3) in such a way that a drop of blood (4) disposed onto slide (1) does not touch the coverglass (2). This is illustrated in FIG. 2. FIG. 2 also shows the slide (1) having an upper surface (6) and a lower surface (7), and the flexible coverglass having an upper surface (8) and a lower surface (9).

FIG. 3 shows the arrangement of FIG. 2 after applying a downward force to the center of coverglass (2) so that coverglass (2) touches the drop of blood (4), and after discontinuing the application of this force. As shown in FIG. 3, coverglass (2) is held in a stable position due to an equilibrium state between adhesion forces and counter forces generated as a consequence of coverglass bending. The drop of blood (4) is spread out, forming then a thin layer (5).

FIGS. 1 to 3 illustrate an arrangement where a standard coverglass, 50 mm×24 mm×160 μm, is positioned above a microscope slide, 75 mm×25 mm×1 mm, using four spacers of 200 μm height. In this particular example, pieces of self-adhesive tape have been used as the spacers. However, the spacers can also be comprised of, for example, rubber, synthetic resin, plastic, wax, glue or other materials. This is a demonstrative example and is not intended in any way to limit the present invention.

The coverglass and microscope slide utilized in any of the embodiments of the present invention can be of any size appropriate to carry out the present invention, and the spacers can have a height of from about 10 μm to about 3000 μm, and more preferably, from about 50 μm to about 200 μm.

It should be noted that although the downward force is applied to the center of the coverglass in the above example, this force can be applied to any area of the coverglass in order to effectuate the method of the present invention.

Figure 4:
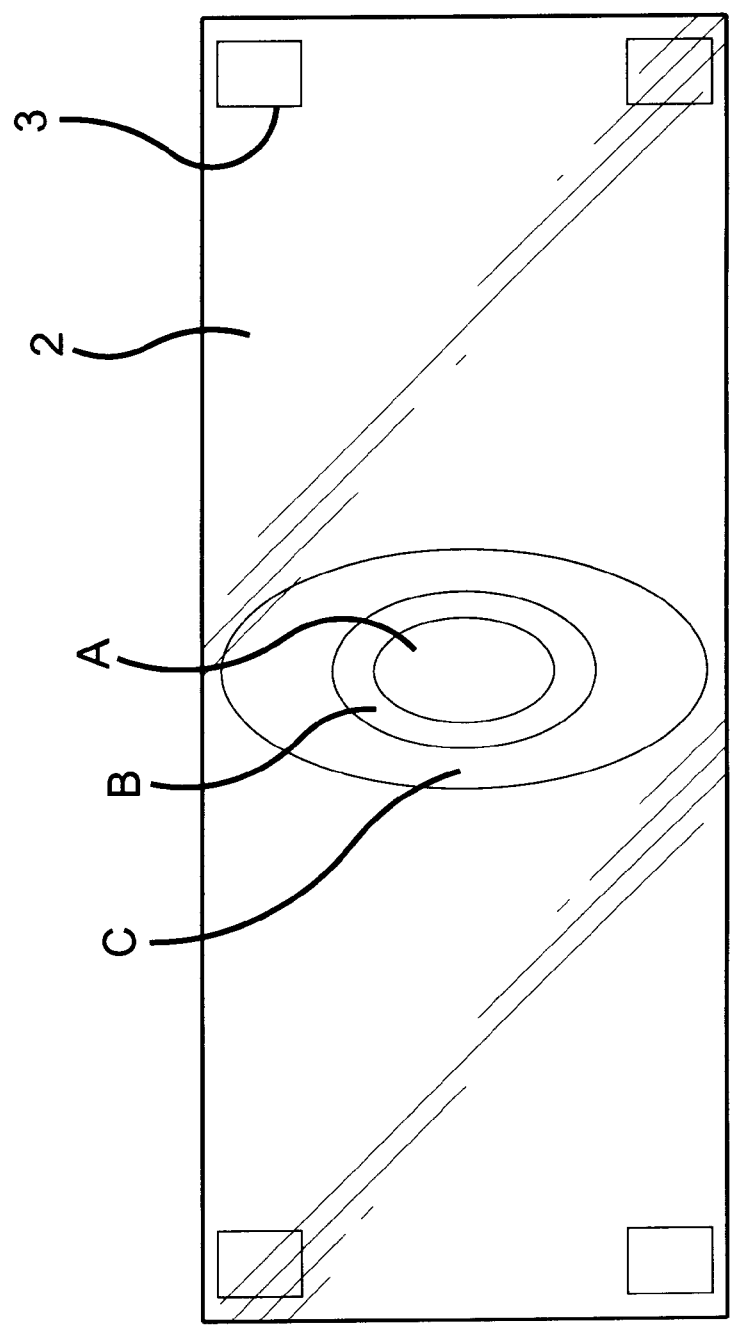
FIG. 4 shows the arrangement of FIG. 3 with a central region containing no red blood cells, a ring containing isolated red blood cells in a monolayer, followed by an outer belt containing red blood cells in Rouleaux formation.

It has been found, as illustrated in FIG. 4, that a liquid blood sample prepared according to the present invention comprises a central area (A) which contains plasma but no red blood cells. Region (A) is surrounded by a wide ring (B) containing huge numbers of isolated red blood cells in a well-defined monolayer arrangement. Ring (B) in turn is surrounded by an even wider belt (C) that contains red blood cells in Rouleaux formation where the length of the Rouleaux blocks increases with increasing distance from the center. This kind of blood sample preparation does not result in morphology changes as observed in the wedge-slide method or during drying of blood films in the open air. Due to the coverglass bending, regions of varying sample thickness are available for examination. It has also been found that a blood sample prepared according to the present invention does not exhibit complex flow patterns or heterogeneous cell distributions as observed with a wedge-shaped sample container.

According to the present invention, it is important that the spread liquid sample, such as blood, fills the space between slide (1) and coverglass (2) only partially. This can be accomplished by selecting the height of the spacers accordingly, as set forth above. In this case, the coverglass is held in a stable position due to an equilibrium state between adhesion forces and counter forces generated as a consequence of coverglass bending.

Figure 5:
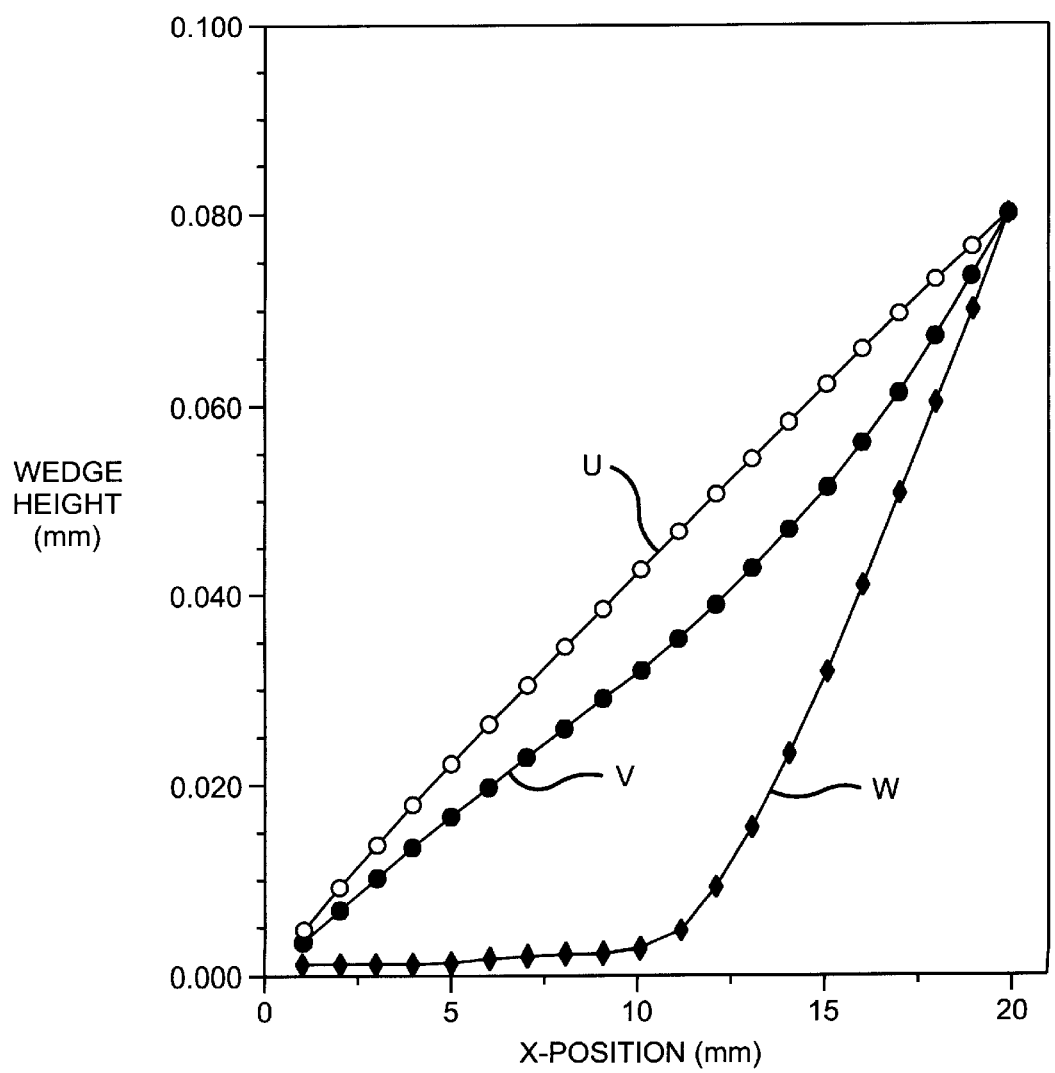
FIG. 5 depicts experimentally observed profiles of wedge sample holders filled either with air, filled with water, or filled partially with water. The wedge height in mm, as measured via the deflection of a laser beam reflected by the coverglass, is shown vs. laser beam position X in mm.

If the liquid sample, such as blood, would fill the space between slide (1) and coverglass (2) totally, then no thin layer of liquid would be generated. As a supporting illustration for this statement, FIG. 5 depicts experimental results obtained on a sample holder where a coverglass and a microscope slide form a wedge due to the fact that the coverglass is resting directly on the slide at one end, and is resting on an 80-μm spacer at the other end. In FIG. 5, curve U shows the wedge profile if the space in between the slide and the coverglass contains only air. This profile has been determined by measuring the deflection of a laser beam reflected by the coverglass as a function of the beam position X, and integrating over all angles. As can be seen, the coverglass shows a small curvature.

Filling the space between the slide and the coverglass totally with water results in a certain deformation of the coverglass, as is shown by curve V in FIG. 5. The deformation is, however, not very strong. A similarly small deformation of the coverglass would happen in a sample compartment according to the present invention. In other words, the thickness of the liquid layer would still be comparable to the height of the spacers used.

Curve W in FIG. 5 shows what happens if the space between the slide and the coverglass is only partially filled with liquid. In this case, strong adhesion forces draw the coverglass towards the slide, forming a very thin layer of liquid sample. This is similar to the situation within a sample prepared according to the present invention. There is, however, a significant difference between a wedge-shaped sample compartment as shown in FIG. 5 and a sample compartment according to the present invention. In a wedge-shaped sample compartment, filling occurs from the thicker end towards the thin end, which results in complex flow patterns and in heterogeneous cell distributions.

Figure 6:
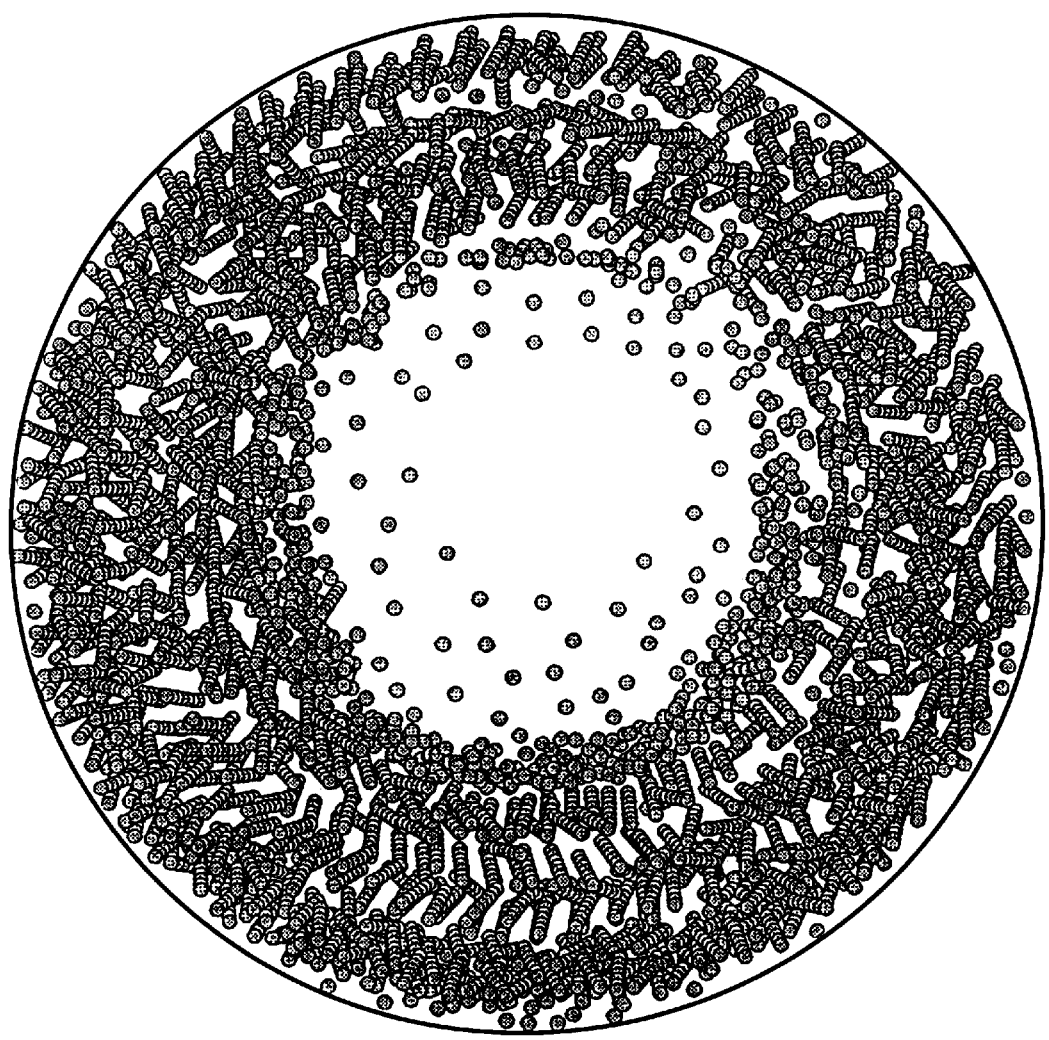
FIG. 6 is a simulated microscopic image showing the central plasma area, the ring of isolated red blood cells, and the outer belt comprising red blood cells in Rouleaux formation as observed under a microscope.
Figure 7:
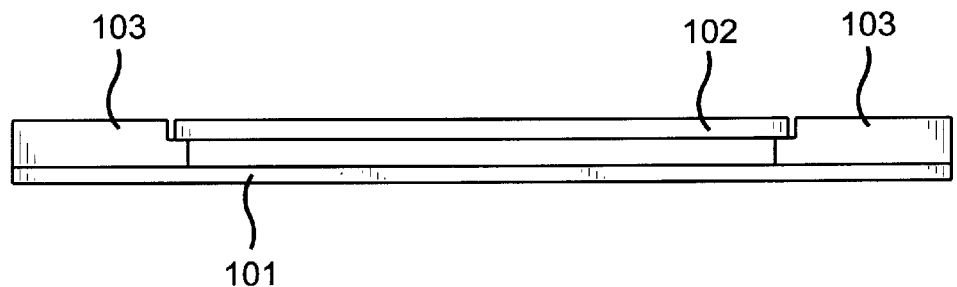
FIG. 7 shows a side view of a microscope slide with a coverglass supported by two spacers.

Filling a sample compartment according to the present invention involves process steps that are quite different. First, the drop of, for example, blood is positioned at the center of the slide, i.e. in the area that later becomes the area for the thinnest liquid layer within the whole sample. In the moment the coverglass touches the drop of blood, the liquid is flowing outwards into all directions. Simultaneously, the thickness of the liquids phase in the center area is constantly decreasing. This process comes to an end when an equilibrium is reached between the adhesion forces and the forces resulting from the deformation of the coverglass that is necessarily involved in this process of filling. As has been mentioned already, this kind of filling does not result in heterogeneous cell distributions. Therefore, the method and device according to the present invention allows for the preparation of excellent blood samples for microscopic analysis. As a further illustration of the method and device for preparing thin liquid samples for microscopic analysis, FIG. 6 is a simulated microscopic image showing the central plasma area, the ring of isolated red blood cells, and the outer belt comprising red blood cells in Rouleaux formation as observed under a microscope.

As stated above, it is within the spirit of the invention to use coverglasses of different sizes (e.g., 24 mm×50 mm, 18 mm×18 mm, 20 mm×20 mm, or the like) and thicknesses (e.g., 160 micrometers, 210 micrometers, or the like), which of course, applies also to the height, the number, and to the positioning of the spacers. As an example, the effective stiffness of a given coverglass can be modified by arranging the spacers not only on the "East" and "West" sides, but in addition on the "North" and "South" sides. The core point is that spacers support the outer edges of the coverglass, while the center is allowed to deform. The arrangement of the spacers at only two opposite sides results in a quasi-cylindrical deformation of the coverglass, which is rather predictable. The spacers can be pre-attached to the slide, or to the coverglass, or a set of spacers can be added as a separate element of the "sandwich-like" sample structure.

The method and device according to the invention always produce, with respect to the preferred embodiment of liquid blood samples, an area that contains mainly blood plasma and no red blood cells. This is a distinct advantage for certain spectroscopic investigations.

The method and device according to the invention are very simple and allow one to prepare samples very quickly. Due to the fact that the coverglass is present, the drying is highly inhibited and cell deformations can be avoided.

In a modification of the invention, the upper surface of the slide and/or the lower surface of the coverglass can carry depositions of specific chemical agents for improving liquid adhesion, preventing blood coagulation, or the like, such as EDTA, acridine orange, TOPRO-3, TOPRO-5, Cy-5, LaJolla Blue or other chemical agents that are sold by Molecular Probes, Inc., Eugene, Oreg.; Fluka Chemical Corp., Milwaukee, Wis. and other companies. In one embodiment, the upper surface of the slide or the lower surface of the coverglass can have at least one well, and further, as many wells as are necessary to carry out the invention, for deposition of at least one or more chemical agents as described above. This is shown in FIGS. 12–16, as discussed in further detail below. In another embodiment, the chemical agent(s) can be spread or dried onto the lower surface of the coverglass or the upper surface of the slide without the use of a well or wells.

As has been mentioned above, the method and device for sample preparation according to the present invention is not limited to blood samples. Thin microscopic samples for many other liquids or suspensions can be produced.

In a further modification of the invention, the coverglass has a deposit of a chemical agent, such as a blood cell lysing agent, that starts a chemical reaction as soon as it comes in contact with a liquid sample which has been deposited on the microscope slide. This modification of the invention allows for monitoring of kinetic processes directly under the microscope.

Further embodiments of the present invention are demonstrated in FIGS. 7–11 and FIGS. 12–16, and are described as follows.

Figure 8:
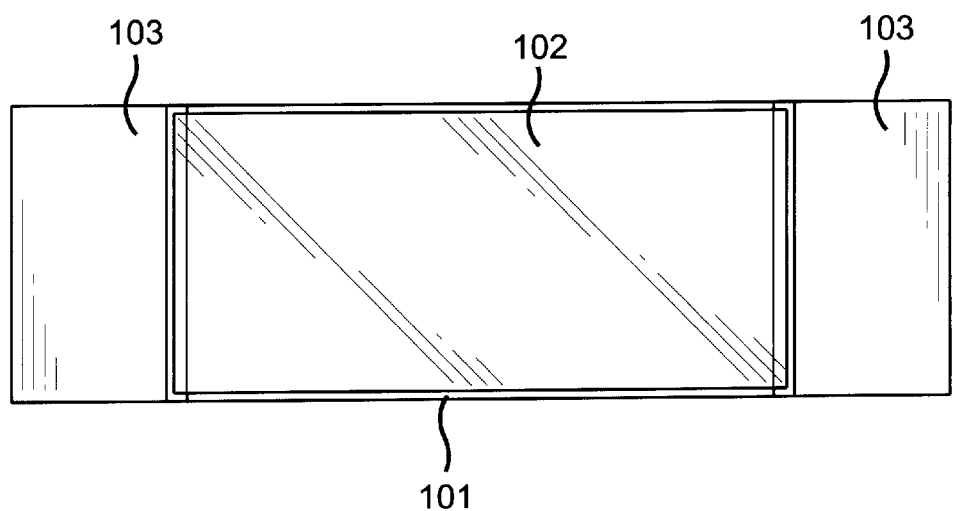
FIG. 8 shows a top plan view of the device of FIG. 7.
Figure 9:
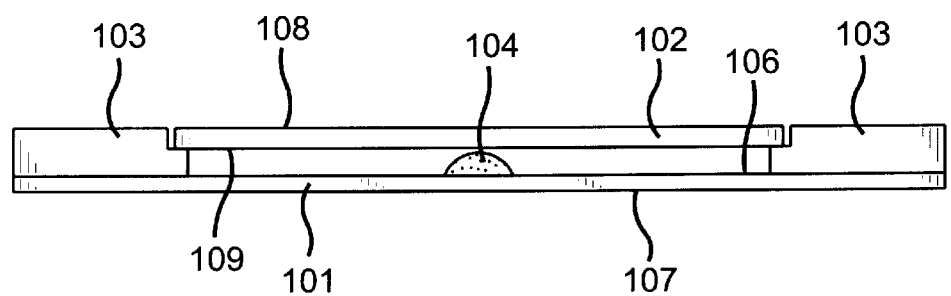
FIG. 9 depicts the arrangement of FIG. 7 with a drop of liquid sample disposed to the center of the slide.

In the embodiment set forth in FIGS. 7–11, two spacers (103) are used to hold a coverglass (102) in a parallel position above a microscope slide (101). The height of the spacers (103) is selected so that the coverglass (102) can be positioned on the spacers (103) in such a way that a drop of liquid sample (104) disposed onto slide (101) does not touch the coverglass (102). This is illustrated in FIG. 9. FIG. 9 also shows the slide (101) having an upper surface (106) and a lower surface (107), and the flexible coverglass having an upper surface (108) and a lower surface (109). FIG. 8 shows a perspective view of the arrangement of FIG. 7.

Figure 10:
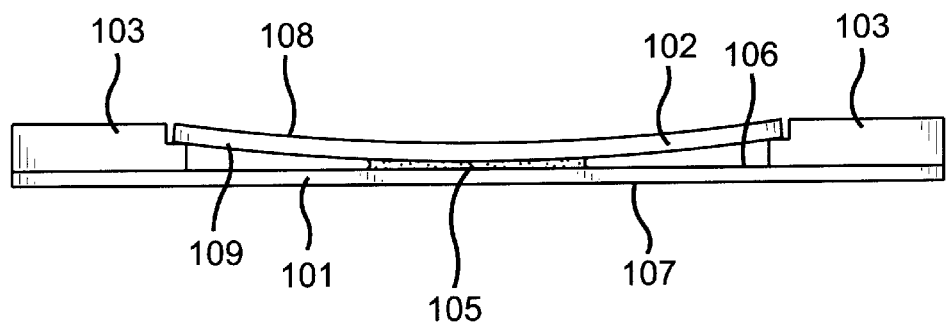
FIG. 10 shows the arrangement of FIG. 9 after applying a downward force to the coverglass and discontinuing the application of this force.
Figure 11:
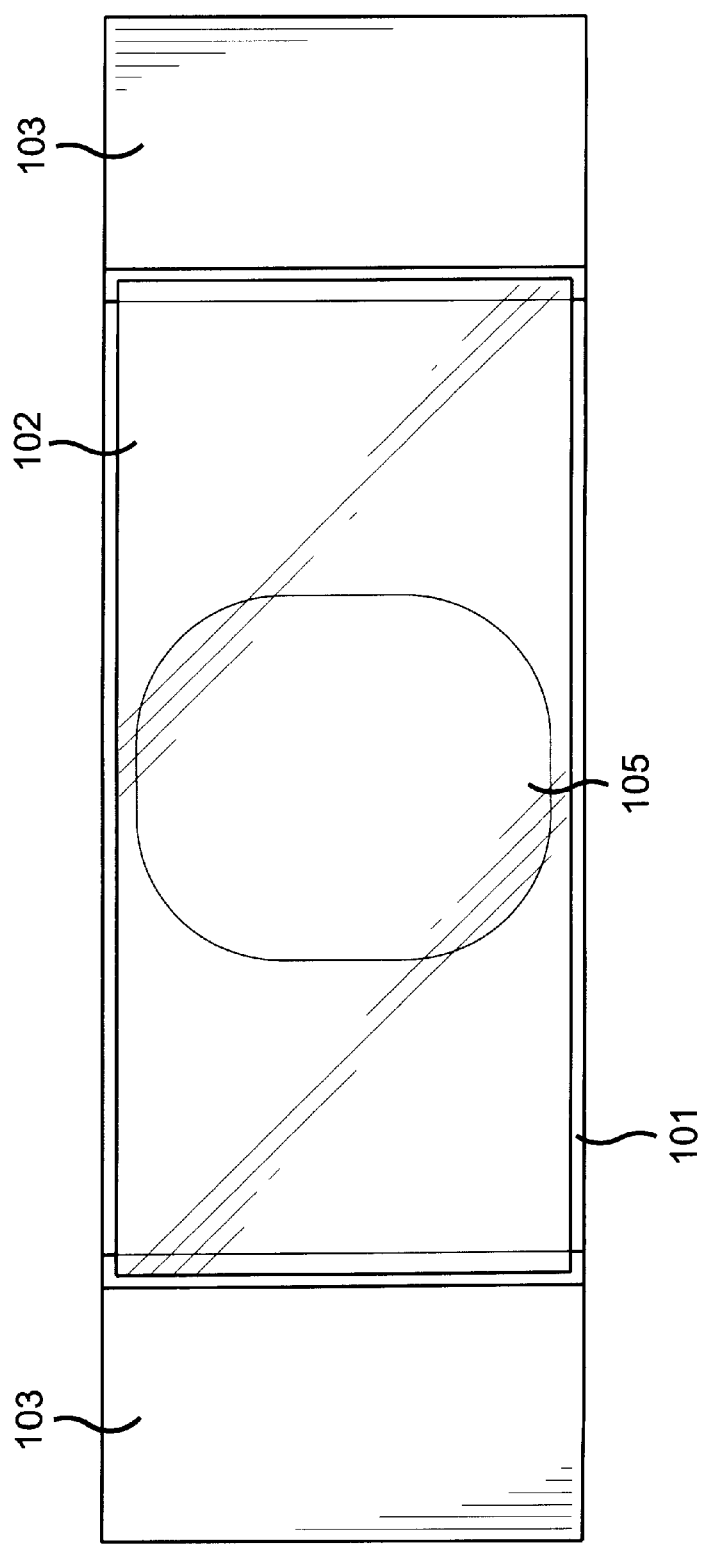
FIG. 11 shows a top plan view of the arrangement of FIG. 10.

FIG. 10 shows the arrangement of FIG. 9 after applying a downward force to the center of coverglass (102) so that coverglass (102) touches the drop of liquid sample (104), and after discontinuing the application of this force. As shown in FIG. 10, the coverglass (102) is held in a stable position due to an equilibrium state between adhesion forces and counter forces generated as a consequence of coverglass bending. The drop of liquid sample (104) is spread out, forming then a thin layer (105). FIG. 11 shows a perspective view of the arrangement of FIG. 10 and thin layer (105).

Figure 12:
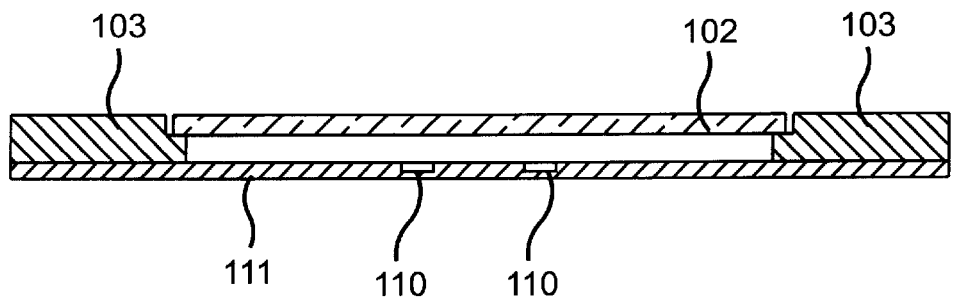
FIG. 12 shows a cross-sectional of a microscope slide having six small wells (only two of the wells can be seen) with a coverglass supported by two spacers.
Figure 13:
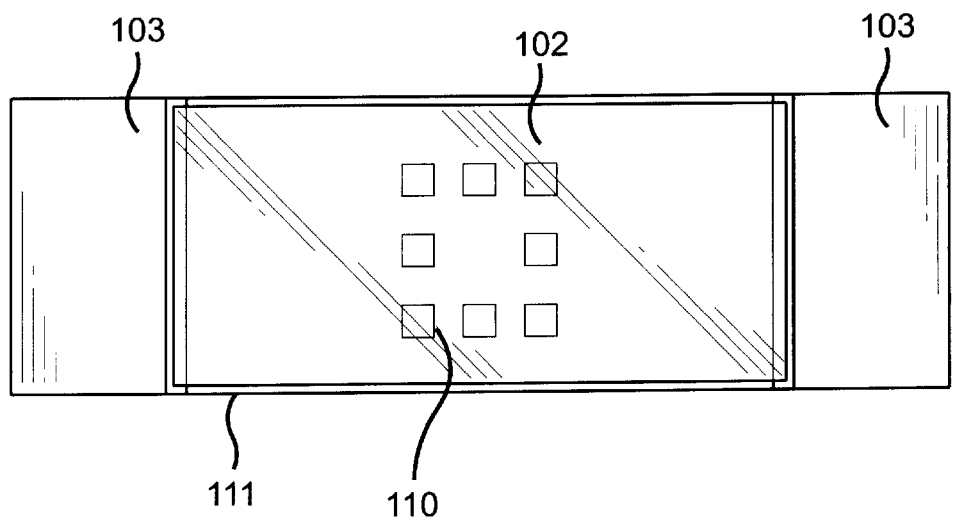
FIG. 13 shows a top plan view of the arrangement of FIG. 12.
Figure 14:
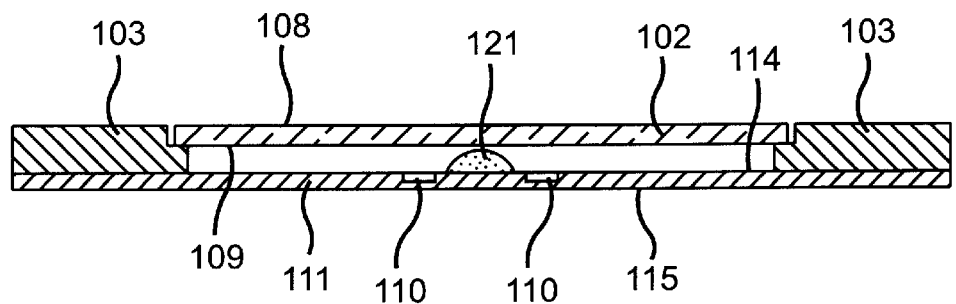
FIG. 14 depicts the arrangement of FIG. 12 with a drop of liquid sample disposed to the center of the slide.

In another embodiment of the present invention as set forth in FIGS. 12–16, a microscope slide (111) is utilized. This microscope slide (111) has, in this embodiment, six wells (110) arranged in the center of the slide for deposition of at least one or more specific chemical agents for improving liquid adhesion, preventing blood coagulation or the like, as identified above. The wells (110) in the microscope slide (111) are shown in FIGS. 12 and 13. FIG. 12, in a side view, shows the two spacers (103) holding the coverglass (102) in a parallel position above the microscope slide (111). As in the previous embodiments of the invention, the height of the spacers (103) is selected so that the coverglass (102) can be positioned on the spacers (103) in such a way that a drop of liquid sample (104) disposed onto slide (111) does not touch the coverglass (102). This is illustrated in FIG. 14. FIG. 14 also shows the slide (111) having an upper surface (114) and a lower surface (115), and the flexible coverglass having an upper surface (108) and a lower surface (109). FIG. 13 shows a perspective view of the arrangement of FIG. 12.

Figure 15:
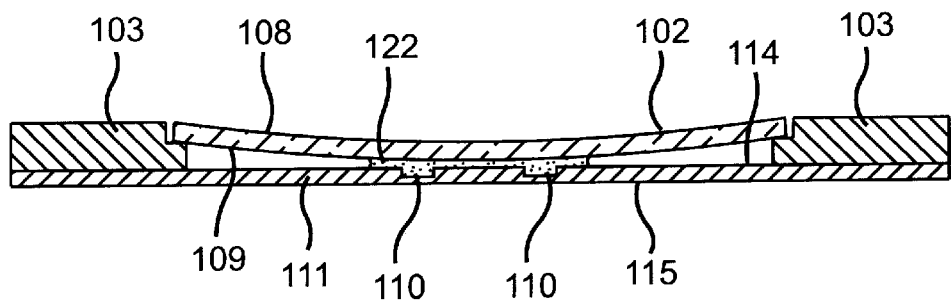
FIG. 15 shows the arrangement of FIG. 14 after applying a downward force to the coverglass and discontinuing the application of this force.
Figure 16:
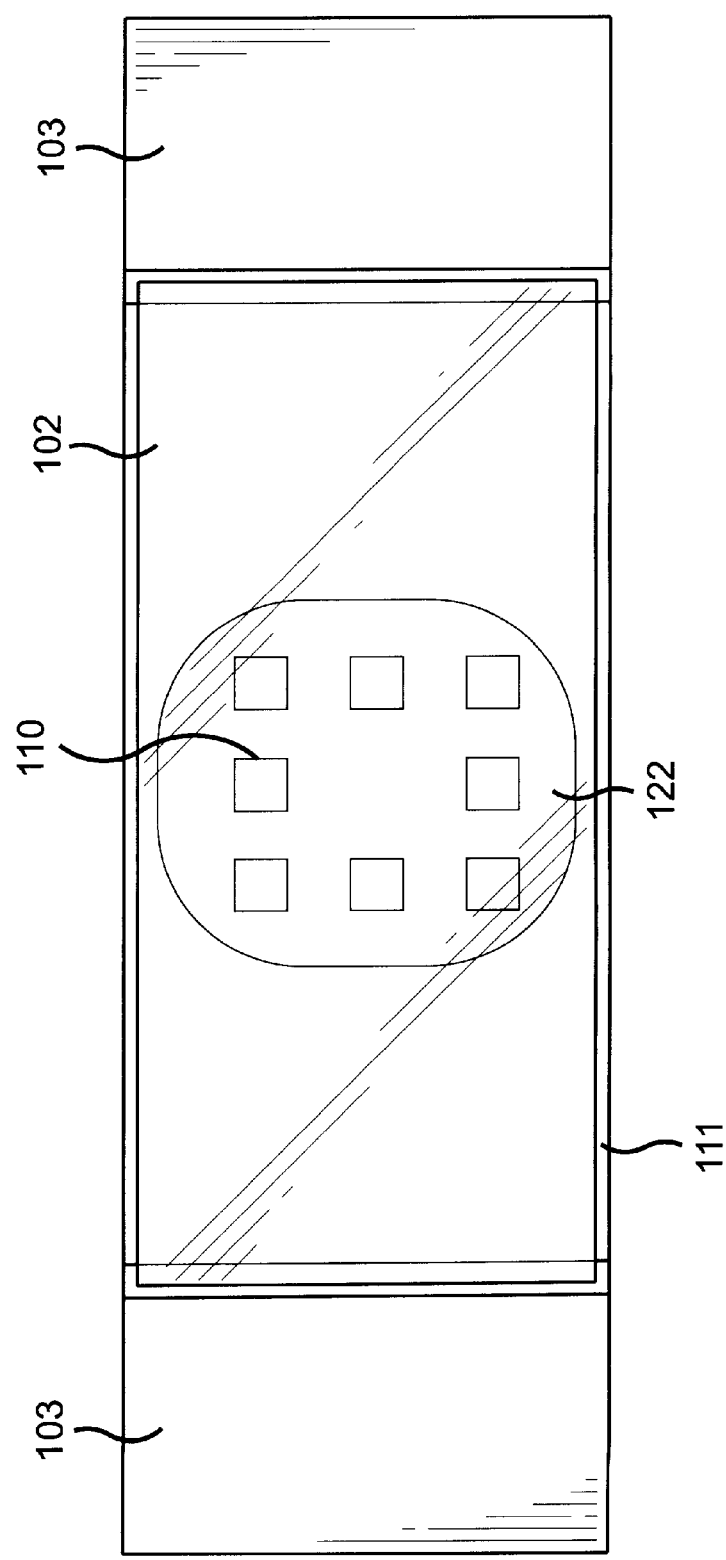
FIG. 16 shows a top plan view of the arrangement of FIG. 15.

FIG. 15 shows the arrangement of FIG. 14 after applying a downward force to the center of coverglass (102) so that coverglass (102) touches the drop of liquid sample (121) and after discontinuing the application of this force. As shown in FIG. 15, the coverglass (102) is held in a stable position due to an equilibrium state between adhesion forces and counter forces generated as a consequence of coverglass bending. The drop of liquid sample (121) is spread out, forming then a thin layer (122) which flows into the wells (110), and these wells (110) have, previously deposited therein, at least one specific chemical agent as described above. FIG. 16 shows a perspective view of the arrangement of FIG. 15, thin layer (122) and the wells (110).

I claim:

1. A method for producing thin samples of liquids for microscopic analysis, in which there is provided:
   (i) a microscope slide having an upper surface and a lower surface, wherein said slide has spacers arranged on the upper surface of the slide outside of the center of the slide; and
   (ii) a flexible coverglass having an upper surface and a lower surface,
   wherein said method comprises:
      a) depositing a drop of a liquid sample onto the upper surface of said microscope slide near to the center of said microscope slide;
      b) positioning the flexible coverglass onto the spacers on the slide;
      c) applying a downward force to the upper surface of the flexible coverglass so that the lower surface of the coverglass touches the sample;
      d) suspending the application of said force; and
      e) obtaining a thin liquid sample.

2. The method of claim 1 wherein said liquid sample is blood.

3. The method of claim 1 wherein said slide has at least two spacers.

4. The method of claim 1 wherein said slide has at least four spacers.

5. The method of claim 3 wherein each spacer has a height of from about 10 $\mu$m to about 3000 $\mu$m.

6. The method of claim 5 wherein each spacer has a height of from about 50 $\mu$m to about 200 $\mu$m.

7. The method of claim 4 wherein each spacer has a height of from about 10 $\mu$m to about 3000 $\mu$m.

8. The method of claim 7 wherein each spacer has a height of from about 50 $\mu$m to about 200 $\mu$m.

9. The method of claim 1 wherein said slide has at least one chemical agent deposited on the upper surface of said slide, prior to deposition of a drop of liquid sample onto said slide.

10. The method of claim 9 wherein said chemical agent is selected from the group consisting of EDTA, acridine orange, TOPRO-3, TOPRO-5, Cy-5, and LaJolla Blue.

11. The method of claim 9 wherein said chemical agent improves liquid adhesion or prevents blood coagulation.

12. The method of claim 9 wherein said chemical agent starts a chemical reaction as soon as it comes in contact with said drop of liquid sample.

13. The method of claim 1 wherein said slide has at least one well disposed to the center of said slide, for deposition of at least one chemical agent, and further, wherein said method further comprises, prior to step (a), depositing at least one chemical agent into said at least one well.

14. The method of claim 13 wherein said chemical agent is selected from the group consisting of EDTA, acridine orange, TOPRO-3, TOPRO-5, Cy-5, and LaJolla Blue.

15. The method of claim 13 wherein said chemical agent improves liquid adhesion or prevents blood coagulation.

16. The method of claim 13 wherein said chemical agent starts a chemical reaction as soon as it comes in contact with said drop of liquid sample.

17. The method of claim 1 wherein said coverglass has at least one chemical agent deposited on the lower surface thereof, prior to deposition of a drop of liquid sample onto said slide.

18. The method of claim 17 wherein said chemical agent is selected from the group consisting of EDTA, acridine orange, TOPRO-3, TOPRO-5, Cy-5, and LaJolla Blue.

19. The method of claim 17 wherein said chemical agent improves liquid adhesion or prevents blood coagulation.

20. The method of claim 17 wherein said chemical agent starts a chemical reaction as soon as it comes in contact with said drop of liquid sample.

21. A method for producing thin samples of liquids for microscopic analysis, in which there is provided:
   (i) a microscope slide having an upper surface and a lower surface; and
   (ii) a flexible coverglass having an upper surface and a lower surface, wherein said coverglass has spacers arranged on the lower surface of the coverglass outside of the center of the coverglass;
   wherein said method comprises:
      a) depositing a drop of a liquid sample onto the upper surface of said microscope slide near to the center of said microscope slide;
      b) positioning the flexible coverglass with the spacers onto the slide;
      c) applying a downward force to the center of the upper surface of the flexible coverglass so that the lower surface of the coverglass touches the sample;
      d) suspending the application of said force; and
      e) obtaining a thin liquid sample.

22. The method of claim 21 wherein said liquid sample is blood.

23. The method of claim 21 wherein said slide has at least two spacers.

24. The method of claim 21 wherein said slide has at least four spacers.

25. The method of claim 23 wherein each spacer has a height of from about 10 $\mu$m to about 3000 $\mu$m.

26. The method of claim 25 wherein each spacer has a height of from about 50 $\mu$m to about 200 $\mu$m.

27. The method of claim 24 wherein each spacer has a height of from about 10 $\mu$m to about 3000 $\mu$m.

28. The method of claim 27 wherein each spacer has a height of from about 50 $\mu$m to about 200 $\mu$m.

29. The method of claim 21 wherein said slide has at least one chemical agent deposited on the upper surface of said slide, prior to deposition of a drop of liquid sample onto said slide.

30. The method of claim 29 wherein said chemical agent is selected from the group consisting of EDTA, acridine orange, TOPRO-3, TOPRO-5, Cy-5, and LaJolla Blue.

31. The method of claim 29 wherein said chemical agent improves liquid adhesion or prevents blood coagulation.

32. The method of claim 29 wherein said chemical agent starts a chemical reaction as soon as it comes in contact with said drop of liquid sample.

33. The method of claim 21 wherein said slide has at least one well disposed to the center of said slide, for deposition of at least one chemical agent, and further, wherein said method further comprises, prior to step (a), depositing at least one chemical agent into said at least one well.

34. The method of claim 33 wherein said chemical agent is selected from the group consisting of EDTA, acridine orange, TOPRO-3, TOPRO-5, Cy-5, and LaJolla Blue.

35. The method of claim 33 wherein said chemical agent improves liquid adhesion or prevents blood coagulation.

36. The method of claim 33 wherein said chemical agent starts a chemical reaction as soon as it comes in contact with said drop of liquid sample.

37. The method of claim 21 wherein said coverglass has at least one chemical agent deposited on the lower surface thereof, prior to deposition of a drop of liquid sample onto said slide.

38. The method of claim 37 wherein said chemical agent is selected from the group consisting of EDTA, acridine orange, TOPRO-3, TOPRO-5, Cy-5, and LaJolla Blue.

39. The method of claim 37 wherein said chemical agent improves liquid adhesion or prevents blood coagulation.

40. The method of claim 37 wherein said chemical agent starts a chemical reaction as soon as it comes in contact with said drop of liquid sample.

41. A method for producing thin samples of liquids for microscopic analysis, in which there is provided:
(i) a microscope slide having an upper surface and a lower surface;
(ii) a flexible coverglass having an upper surface and a lower surface; and
(iii) spacers, to be positioned between said slide and said flexible coverglass;
wherein said method comprises:
a) depositing a drop of a liquid sample onto the upper surface of said microscope slide near to the center of said microscope slide;
b) positioning the spacers between the slide and the flexible coverglass;
c) positioning the flexible coverglass onto the spacers;
d) applying a downward force to the upper surface of the flexible coverglass so that the lower surface of the coverglass touches the sample;
e) suspending the application of said force; and
f) obtaining a thin liquid sample.

42. The method of claim 41 wherein said liquid sample is blood.

43. The method of claim 41 wherein said slide has at least two spacers.

44. The method of claim 41 wherein said slide has at least four spacers.

45. The method of claim 43 wherein each spacer has a height of from about 10 $\mu$m to about 3000 $\mu$m.

46. The method of claim 45 wherein each spacer has a height of from about 50 $\mu$m to about 200 $\mu$m.

47. The method of claim 44 wherein each spacer has a height of from about 10 $\mu$m to about 3000 $\mu$m.

48. The method of claim 47 wherein each spacer has a height of from about 50 $\mu$m to about 200 $\mu$m.

49. The method of claim 41 wherein said slide has at least one chemical agent deposited on the upper surface of said slide, prior to deposition of a drop of liquid sample onto said slide.

50. The method of claim 49 wherein said chemical agent is selected from the group consisting of EDTA, acridine orange, TOPRO-3, TOPRO-5, Cy-5, and LaJolla Blue.

51. The method of claim 49 wherein said chemical agent improves liquid adhesion or prevents blood coagulation.

52. The method of claim 49 wherein said chemical agent starts a chemical reaction as soon as it comes in contact with said drop of liquid sample.

53. The method of claim 41 wherein said slide has at least one well disposed to the center of said slide, for deposition of at least one chemical agent, and further, wherein said method further comprises, prior to step (a), depositing at least one chemical agent into said at least one well.

54. The method of claim 53 wherein said chemical agent is selected from the group consisting of EDTA, acridine orange, TOPRO-3, TOPRO-5, Cy-5, and LaJolla Blue.

55. The method of claim 53 wherein said chemical agent improves liquid adhesion or prevents blood coagulation.

56. The method of claim 53 wherein said chemical agent starts a chemical reaction as soon as it comes in contact with said drop of liquid sample.

57. The method of claim 41 wherein said coverglass has at least one chemical agent deposited on the lower surface thereof, prior to deposition of a drop of liquid sample onto said slide.

58. The method of claim 57 wherein said chemical agent is selected from the group consisting of EDTA, acridine orange, TOPRO-3, TOPRO-5, Cy-5, and LaJolla Blue.

59. The method of claim 57 wherein said chemical agent improves liquid adhesion or prevents blood coagulation.

60. The method of claim 57 wherein said chemical agent starts a chemical reaction as soon as it comes in contact with said drop of liquid sample.

* * * * *